United States Patent
Matsui (10) Patent No.: US 8,421,853 B2
(45) Date of Patent: Apr. 16, 2013

(54) CAPSULE ENDOSCOPE SYSTEM (75) Inventor: Akira Matsui, Hino (JP)

(73) Assignee: Olympus Corporation, Tokyo (JP)

( * ) Notice: Subject to any disclaimer, the term of this patent is extended or adjusted under 35 U.S.C. 154(b) by 1468 days.

(21) Appl. No.: 11/662,670

(22) PCT Filed: Sep. 14, 2005

(86) PCT No.: PCT/JP2005/016974
§ 371 (c)(1), (2), (4) Date: Mar. 13, 2007

(87) PCT Pub. No.: WO2006/030839
PCT Pub. Date: Mar. 23, 2006

(65) Prior Publication Data
US 2008/0074491 A1    Mar. 27, 2008

(30) Foreign Application Priority Data
Sep. 16, 2004    (JP) .................................. 2004-269570

(51) Int. Cl.
*H04N 7/18* (2006.01)

(52) U.S. Cl.
USPC .............................................. 348/77; 348/65

(58) Field of Classification Search .................... 348/45, 348/61, 65, 73–77, 246–247
See application file for complete search history.

(56) References Cited

U.S. PATENT DOCUMENTS

| | | | |
|---|---|---|---|
| 4,480,636 A | 11/1984 | Karaki et al. | |
| 5,604,531 A | 2/1997 | Iddan et al. | |
| 6,026,200 A * | 2/2000 | Okude et al. | 382/311 |
| 6,104,839 A | 8/2000 | Cok et al. | |
| 6,190,308 B1 * | 2/2001 | Irion et al. | 600/109 |
| 2001/0051766 A1 | 12/2001 | Gazdzinski | |
| 2002/0048322 A1 * | 4/2002 | Yamamoto et al. | 375/240.12 |
| 2003/0058998 A1 * | 3/2003 | Aufrichtig et al. | 378/207 |
| 2003/0213495 A1 | 11/2003 | Fujita | |
| 2003/0222995 A1 * | 12/2003 | Kaplinsky et al. | 348/247 |
| 2004/0027459 A1 | 2/2004 | Segawa et al. | |

(Continued)

FOREIGN PATENT DOCUMENTS

| | | |
|---|---|---|
| EP | 1 003 332 A2 | 5/2000 |
| EP | 1 610 485 A2 | 12/2005 |

(Continued)

OTHER PUBLICATIONS

European Search Report dated Dec. 5, 2011 from corresponding European Patent Application No. EP 11 00 8311.0.

(Continued)

*Primary Examiner* — Joshua Joo
(74) *Attorney, Agent, or Firm* — Scully Scott Murphy & Presser, PC (57) ABSTRACT

To provide a capsule endoscope system capable of easily detecting or correcting a communication error, without increasing power consumption of the capsule endoscope. The capsule endoscope system includes a receiving apparatus that has a pixel defect corrector. The receiving apparatus receives a radio signal that includes image data imaged by a capsule endoscope inserted into an internal portion of a subject, and acquires the image data based on the received radio signal. The pixel defect corrector detects a pixel defect of the image data based on a pixel value of each pixel that configures the acquired image data, and corrects the detected pixel defect.

2 Claims, 6 Drawing Sheets

U.S. PATENT DOCUMENTS

| | | | |
|---|---|---|---|
| 2004/0169746 A1* | 9/2004 | Chen et al. | 348/246 |
| 2005/0030395 A1* | 2/2005 | Hattori | 348/246 |
| 2005/0030412 A1* | 2/2005 | Nakayama | 348/362 |
| 2005/0047658 A1* | 3/2005 | Kita | 382/167 |
| 2005/0049461 A1* | 3/2005 | Honda et al. | 600/160 |
| 2005/0078204 A1* | 4/2005 | Matsuoka et al. | 348/247 |
| 2005/0146621 A1* | 7/2005 | Tanaka et al. | 348/211.2 |
| 2007/0285536 A1* | 12/2007 | Post | 348/247 |

FOREIGN PATENT DOCUMENTS

| | | |
|---|---|---|
| EP | 1 637 046 A1 | 3/2006 |
| EP | 1 637 064 A1 | 3/2006 |
| JP | 63-132588 A | 6/1988 |
| JP | 05-068209 | 3/1993 |
| JP | 9-18790 A | 1/1997 |
| JP | 2001-148862 | 5/2001 |
| JP | 2001-231186 | 8/2001 |
| JP | 2001-345964 A | 12/2001 |
| JP | 2003-79569 A | 3/2003 |
| JP | 2003-325439 A | 11/2003 |
| JP | 2004-154176 | 6/2004 |
| JP | 2004-248753 | 9/2004 |
| JP | 2004-358094 | 12/2004 |
| JP | 2005-205071 | 8/2005 |
| WO | WO 03/024094 * | 3/2003 |
| WO | WO 2004/112593 A1 | 12/2004 |

OTHER PUBLICATIONS

Summons to attend Oral Proceedings dated Feb. 20, 2012 from corresponding European Patent Application No. EP 05 783 112.5.

Japanese Office Action dated Aug. 28, 2012 from corresponding Japanese Patent Application No. JP 2010-256106, together with an English language translation.

Decision of a Patent Grant dated Dec. 4, 2012 from corresponding Japanese Patent Application No. JP 2010-256106, together with an English language translation.

* cited by examiner

CAPSULE ENDOSCOPE SYSTEM

TECHNICAL FIELD

The present invention relates to a capsule endoscope system using a receiving apparatus for receiving image data imaged by a capsule endoscope inserted into the interior of a subject body via a predetermined radio wave from the capsule endoscope.

BACKGROUND ART

Recently, in the field of endoscopes, there are capsule endoscopes, which are swallowable endoscopes provided with an imaging function and a radio communication function, and a capsule endoscope system for acquiring in-vivo image data imaged by the capsule endoscope has been under development. In the capsule endoscope system, the capsule endoscope is swallowed from a mouth of the subject for observation (examination) and is naturally discharged from the subject. During that time, the capsule endoscope moves in the interior of the subject such as the interior of internal organs including a stomach and a small intestine according to the peristaltic activity, and at the same time, the capsule endoscope images the interior of the subject at predetermined intervals such as at intervals of 0.5 second.

While the capsule endoscope moves in the interior of the subject, the image data imaged by the capsule endoscope is sequentially transmitted to the exterior by a radio communication. A receiving apparatus receives the image data via a receiving antenna provided outside. The receiving apparatus generates the image data based on a radio signal sequentially received via the receiving antenna. Through this process, the in-vivo image data imaged by the capsule endoscope is acquired. The receiving apparatus sequentially stores the acquired image data into its memory. The subject carries the receiving apparatus having the radio communication function and the memory function so as to freely move while the subject swallows the capsule endoscope and naturally discharges it. Thereafter, a doctor or a nurse takes out the image data stored in the memory of the receiving apparatus and feeds it to a display device. The display device then displays on its display the in-vivo image such as an image of internal organs based on the obtained image data. A doctor or a nurse can perform a diagnosis of the subject using the image of internal organs or the like displayed on the display (see, for example, Patent Document 1).

In such capsule endoscope system, the capsule endoscope transmits various kinds of data such as image data to the receiving apparatus by transmitting a radio signal to the receiving apparatus. It is probable that a communication error occurs due to noise or the like while the radio signal is being communicated. A generally used method for detecting and correcting such communication error includes a method in which the capsule endoscope, which is a data transmission side, calculates an error correction code regarding the data to be transmitted, adds the error correction code to the data supposed to be transmitted, and transmits it. The receiving apparatus receives the data transmitted from the capsule endoscope, and at the same time, detects and corrects the error of the received data, based on the error correction code added to the received data.

Patent Document 1: Japanese Patent Application Laid-open No. 2001-231186

DISCLOSURE OF INVENTION

Problem to be Solved by the Invention

However, in the capsule endoscope system described above, when the capsule endoscope, which is a transmission apparatus, performs a process in which the above error correction code is calculated and the error correction code is added to the data to be transmitted, the size of an internal circuit of the capsule endoscope increases. As a result, power consumption of the capsule endoscope increases.

The present invention has been achieved in view of the above, and an object of the present invention is to provide a capsule endoscope system capable of easily detecting or correcting a communication error without increasing power consumption of the capsule endoscope main body.

Means for Solving Problem

A capsule endoscope system according to one aspect of the present invention includes a capsule endoscope that images image data of a subject, and transmits a radio signal that includes the image data of which a pixel defect is not corrected, and a receiving apparatus that receives the radio signal to acquire the image data based on the radio signal received, and that includes a pixel defect corrector that detects and corrects a pixel defect of the image data.

Furthermore, in the capsule endoscope system, the capsule endoscope may transmit the radio signal in an uncompressed state.

Further, a capsule endoscope system according to another aspect of the present invention includes a capsule endoscope that is inserted into an interior of a subject, images image data of the interior of the subject, and transmits a radio signal that includes the image data, and a receiving apparatus that receives the radio signal and acquires the image data based on the radio signal received, wherein the capsule endoscope includes a parameter storage unit that stores specific information of the capsule endoscope, and a transmitter that transmits the radio signal that includes the image data and the specific information included in each line, wherein at least one portion of the specific information is included in each line, which serves as a unit of transmission at the time of transmission of the image data, and the receiving apparatus includes a control unit that determines whether the image data is effective or ineffective, based on the specific information included in the each line.

Further, a capsule endoscope system according to still another aspect of the present invention includes a capsule endoscope that images image data of a subject, and transmits a radio signal that includes the image data of which a pixel defect is not corrected and a pixel defect address, and a receiving apparatus that receives the radio signal to acquire the image data and the pixel defect address based on the radio signal received, and that includes a pixel defect corrector that corrects based on the pixel defect address.

Further, a capsule endoscope system according to still another aspect of the present invention includes a capsule endoscope that images image data of a subject, and transmits a radio signal that includes the image data of which a pixel defect is corrected, and a receiving apparatus that receives the radio signal to acquire the image data based on the radio signal received, and that includes a pixel defect corrector that detects and corrects a communication error of a pixel unit in the image data similarly to the pixel defect.

Further, a capsule endoscope system according to still another aspect of the present invention includes a capsule endoscope that images image data of a subject, and transmits a radio signal that includes the image data of which a pixel defect is not corrected, and a receiving apparatus that receives the radio signal to acquire the image data based on the radio signal received, and that includes a pixel defect corrector that detects and corrects a pixel defect and a communication error of a pixel unit in the image data.

Further, a method according to still another aspect of the present invention includes imaging image data of a subject using a capsule endoscope; transmitting a radio signal that includes the image data of which a pixel defect is not corrected from the capsule endoscope; receiving the radio signal using a receiving apparatus to acquire the image data based on the radio signal received; and detecting and correcting a pixel defect of the image data received.

In the above method, the radio signal may be transmitted in an uncompressed state.

Further, a method according to still another aspect of the present invention includes imaging image data of an interior of a subject using a capsule endoscope which is inserted into the interior of the subject and in which specific information is stored; transmitting a radio signal from the capsule endoscope, the radio signal including the image data and the specific information included in each line, at least one portion of the specific information being included in each line, which serves as a unit of transmission at the time of transmission of the image data; receiving the radio signal using a receiving apparatus to acquire the image data based on the radio signal received; and determining whether the image data is effective or ineffective, based on the specific information included in the each line.

Further, a method according to still another aspect of the present invention includes imaging image data of a subject using a capsule endoscope; transmitting a radio signal that includes the image data of which a pixel defect is not corrected and a pixel defect address from the capsule endoscope; receiving the radio signal using a receiving apparatus to acquire the image data and the pixel defect address based on the radio signal received; and correcting based on the pixel defect address.

Further, a method according to still another aspect of the present invention includes imaging image data of a subject using a capsule endoscope; transmitting a radio signal that includes the image data of which a pixel defect is corrected from the capsule endoscope; receiving the radio signal using a receiving apparatus to acquire the image data based on the radio signal received; detecting and correcting a communication error of a pixel unit in the image data similarly to the pixel defect.

Further, a method according to still another aspect of the present invention includes imaging image data of a subject using a capsule endoscope; transmitting a radio signal that includes the image data of which a pixel defect is not corrected from the capsule endoscope; receiving the radio signal using a receiving apparatus to acquire the image data based on the radio signal received; and detecting and correcting a pixel defect and a communication error of a pixel unit in the image data.

Effect of the Invention

According to the present invention, it is possible to achieve a capsule endoscope using a receiving apparatus capable of detecting a communication error caused by noise interference that a radio signal from a capsule endoscope suffers on its propagation path, or interference with a different radio signal, without increasing power consumption of the capsule endoscope, and easily correcting the detected communication error.

EXPLANATIONS OF LETTERS OR NUMERALS

1 Subject
2 Capsule endoscope
3 Receiving apparatus
3a to 3h Receiving antenna
4 Display device
5 Portable recording medium
20 Illuminating unit
21 Illuminating unit driving circuit
22 Imaging unit
23 Imaging unit driving circuit
24, 32 Image processor
25 Parameter storage unit
26 Transmitting circuit
27 Transmitting antenna
28, 33 Control unit
29, 35 Power supply unit
30 Antenna selector
31 Receiving circuit
34 Storage unit
321 Signal separator
322 Pixel defect corrector
322a Pixel defect detector
323 Parameter detector
324 Image signal processing unit
325 Image compressing unit
D1 Horizontal identifying data
D2 Capsule ID data
D3 WB data
D4 Image data

BEST MODE(S) FOR CARRYING OUT THE INVENTION

Exemplary embodiments of a receiving apparatus and a capsule endoscope system according to the present invention will be explained below in detail with reference to the accompanying drawings. Note that the invention is not limited to the embodiments.

Figure 1:
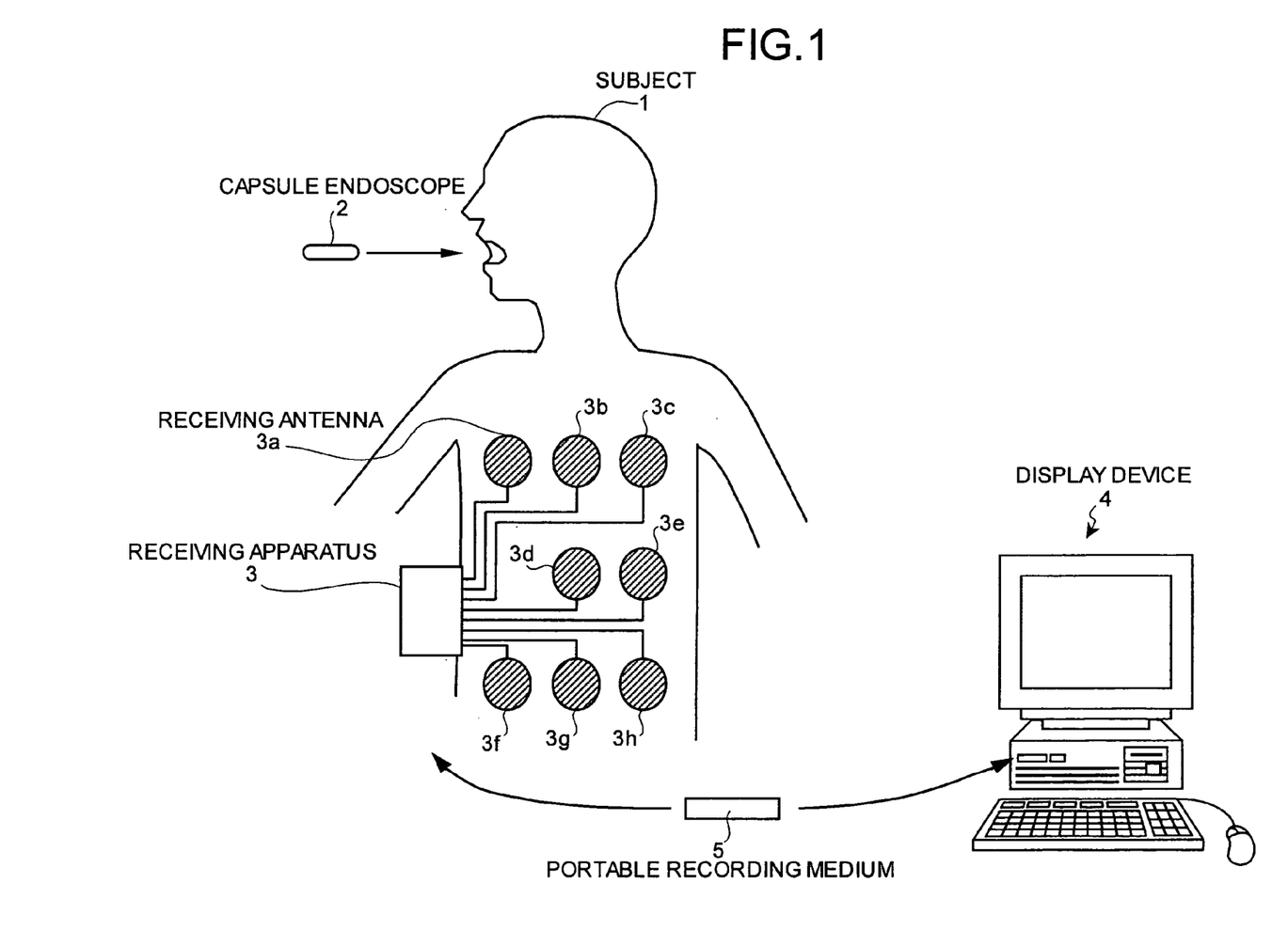
FIG. 1 is a schematic diagram of a configuration example of a capsule endoscope system according to one embodiment of the present invention.

FIG. 1 is a schematic diagram of a configuration example of a capsule endoscope system according to one embodiment of the present invention. As shown in FIG. 1, the capsule endoscope system includes a capsule endoscope 2 that moves along a passage channel in a subject 1 and images the interior of the subject body 1, a receiving apparatus 3 that receives image data imaged by the capsule endoscope 2, a display device 4 that displays the image of the interior of the subject 1 based on the image data imaged by the capsule endoscope 2, and a portable recording medium 5 for exchanging information between the receiving apparatus 3 and the display device 4. The receiving apparatus 3 includes receiving antennas 3a to 3h for receiving a radio signal transmitted by the capsule endoscope 2.

The function of the display device 4 is to display in-vivo images or the like of the subject 1 imaged by the capsule endoscope 2, and has a configuration like a workstation for displaying an image based on the image data and the like obtained via the portable recording medium 5. The image includes an image of internal organs of the subject 1, for example. The display device 4 can display the image on a CRT display or a liquid crystal display or the like, and can also output the image to another medium such as a printer. The display device 4 has a processing function for a doctor or a nurse to perform a diagnosis based on the in-vivo image of the subject such as an image of internal organs or the like, imaged by the capsule endoscope 2.

The portable recording medium 5 is a portable recording medium such as Compact Flash (Registered Trademark) or a smart media. The portable recording medium 5 is attachable to and detachable from the receiving apparatus 3 and the display device 4, and has a structure to enable outputting and recording of information upon attachment to the receiving apparatus 3 and the display device 4. More specifically, upon attachment to the receiving apparatus 3, the portable recording medium 5 can sequentially store the in-vivo image data of the subject 1 or the like received by the receiving apparatus 3 from the capsule endoscope 2. After the capsule endoscope 2 is discharged from the subject 1, the portable recording medium 5 is taken out from the receiving apparatus 3, and attached to the display device 4. The stored image data or the like are read out by the display device 4. Unlike the case of a cable connection between the receiving apparatus 3 and the display device 4, the data exchange between the receiving apparatus 3 and the display device 4 by the portable recording medium 5 provides a free movement to the subject 1 with the receiving apparatus 3 being carried even when the capsule endoscope 2 is in the middle of movement in the interior of the subject 1.

The capsule endoscope 2 is swallowed by the subject 1, passes through the esophagus in the subject 1, and proceeds in the body cavity by peristalsis of the lumen of gastrointestinal. At the same time, the capsule endoscope 2 sequentially images the in-vivo image of the subject 1, and sequentially transmits to the receiving apparatus 3 side the obtained in-vivo image data of the subject 1.

Figure 2:
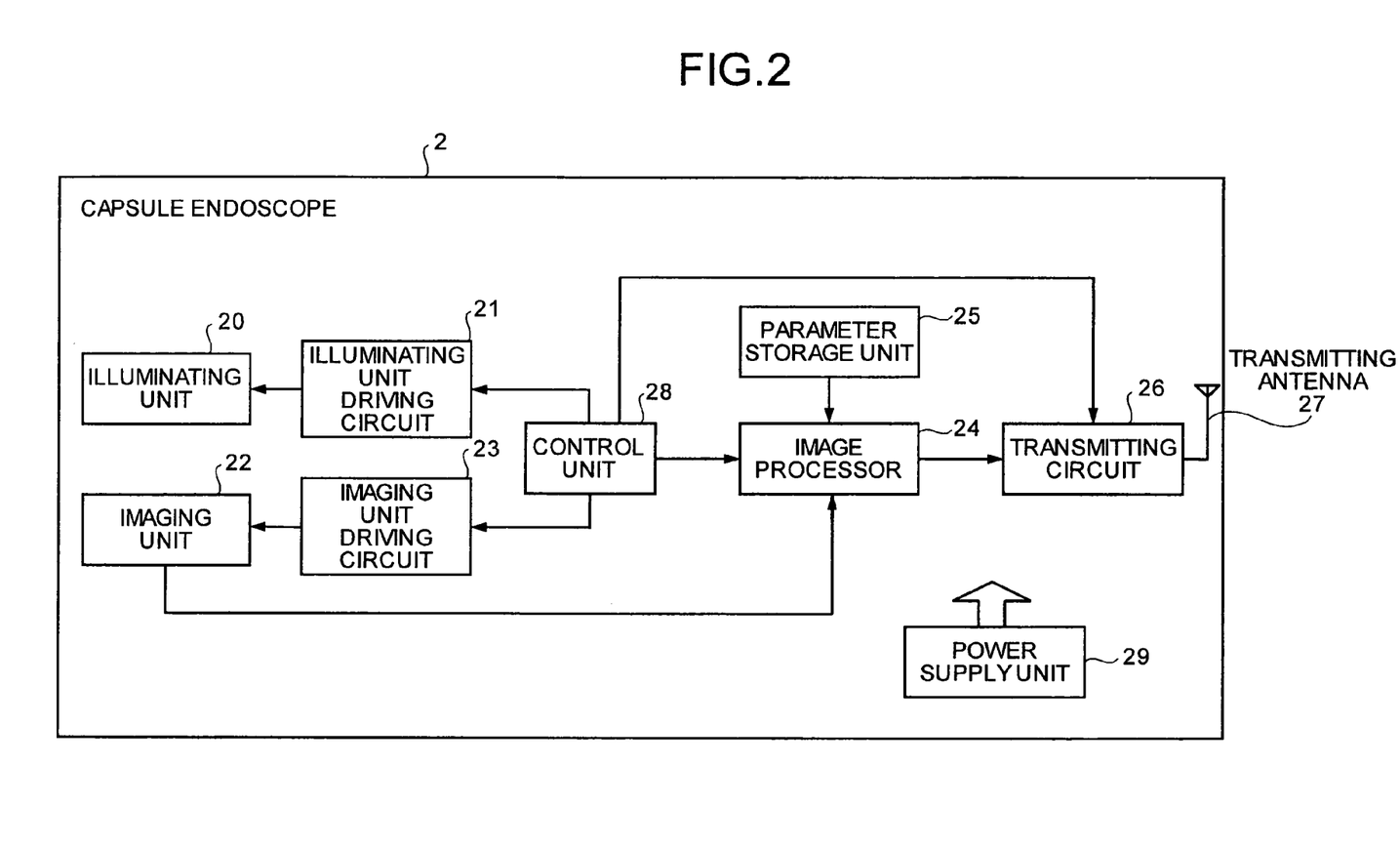
FIG. 2 is a block diagram of a configuration example of a capsule endoscope system including a capsule endoscope.

FIG. 2 is a block diagram of a configuration example of the capsule endoscope 2. The capsule endoscope 2 includes an illuminating unit 20 that illuminates an imaging region when the interior of the subject 1 is imaged, an illuminating unit driving circuit 21 for controlling driving of the illuminating unit 20, an imaging unit 22 that images a reflected optical image from the region illuminated by the illuminating unit 20, and an imaging unit driving circuit 23 for controlling driving of the imaging unit 22. The capsule endoscope 2 further includes an image processor 24 that generates an image signal on which the image data imaged by the imaging unit 22 and a parameter such as white balance data (WB data) or the like are superimposed, a parameter storage unit 25 that stores the parameter beforehand, a transmitting circuit 26 for modulating the image signal generated by the image processor 24 so as to generate a radio signal, a transmitting antenna 27 for outputting to the exterior the radio signal output from the transmitting circuit 26, a control unit 28 that controls the illuminating unit driving circuit 21, the imaging unit driving circuit 23, the image processor 24, and the transmitting circuit 26, and a power supply unit 29 that supplies driving power to each constituent element.

The illuminating unit 20 is achieved by a light emitting element such as LED or the like. The illuminating unit 20 outputs irradiating light so as to illuminate a region imaged by the imaging unit 22. The imaging unit 22 is achieved by an image pickup device such as CCD, CMOS or the like, and receives reflection light from the region illuminated by the illuminating unit 20 so as to image an image in the region. The imaging unit 22 outputs the obtained image data to the image processor 24. The control unit 28 controls the illuminating unit driving circuit 21 and the imaging unit driving circuit 23 so that an illuminating timing of the imaging region by the illuminating unit 20 and an imaging timing of the imaging region by the imaging unit 22 are synchronized.

The image processor 24 generates an image signal that includes the image data imaged by the imaging unit 22. In this case, the image processor 24 generates the image signal without compressing the image data. The parameter storage unit 25 is achieved by a nonvolatile memory IC such as EPROM. An image-data related parameter, such as WB data and capsule ID data specific to the capsule endoscope 2 is recorded beforehand in the parameter storage unit 25. The image processor 24 reads out the capsule ID data and the WB data stored in the parameter storage unit 25, and generates an image signal in which the read-out capsule ID data and WB data, and non-compressed image data are superimposed. The image processor 24 transmits the generated image signal to the transmitting circuit 26. The capsule ID data is information specific to the capsule endoscope 2. More specifically, the capsule ID data is specific information for specifying the capsule endoscope 2.

The transmitting circuit 26 performs a predetermined modulation process, a power amplifying process, for example, on the image signal generated by the image processor 24 so as to generate a radio signal that corresponds to the image signal. The radio signal includes the non-compressed image data. The transmitting circuit 26 outputs the generated radio signal to the transmitting antenna 27. The transmitting antenna 27 outputs to the exterior the radio signal fed from the transmitting circuit 26. The capsule endoscope 2 is to output to the exterior the radio signal that includes the non-compressed image data (non-compression state).

The receiving apparatus 3 is explained next. The receiving antennas 3a to 3h are electrically connected to the receiving apparatus 3, as explained above. The receiving antennas 3a to 3h are achieved by a loop antenna, for example. The receiving antennas 3a to 3h are arranged in predetermined positions on the body surface of the subject 1, for example, in positions corresponding to a passage channel of the capsule endoscope 2, as shown in FIG. 1. The function of the receiving antennas 3a to 3h is to receive the radio signal transmitted by the capsule endoscope 2 in this arrangement. Note that the number of the receiving antennas electrically connected to the receiving apparatus 3 is one or more, preferably plural, and it is not particularly limited to four.

The function of the receiving apparatus 3 is to perform a receiving process of the radio signal received via any one of the receiving antennas 3a to 3h. Owing to the plurality of receiving antennas arranged in the subject 1, the receiving apparatus 3 can acquire the image data by the capsule endoscope 2 via a receiving antenna arranged in a position appropriate for receiving the radio signal, corresponding to the position of the capsule endoscope 2 in the subject 1.

Figure 3:
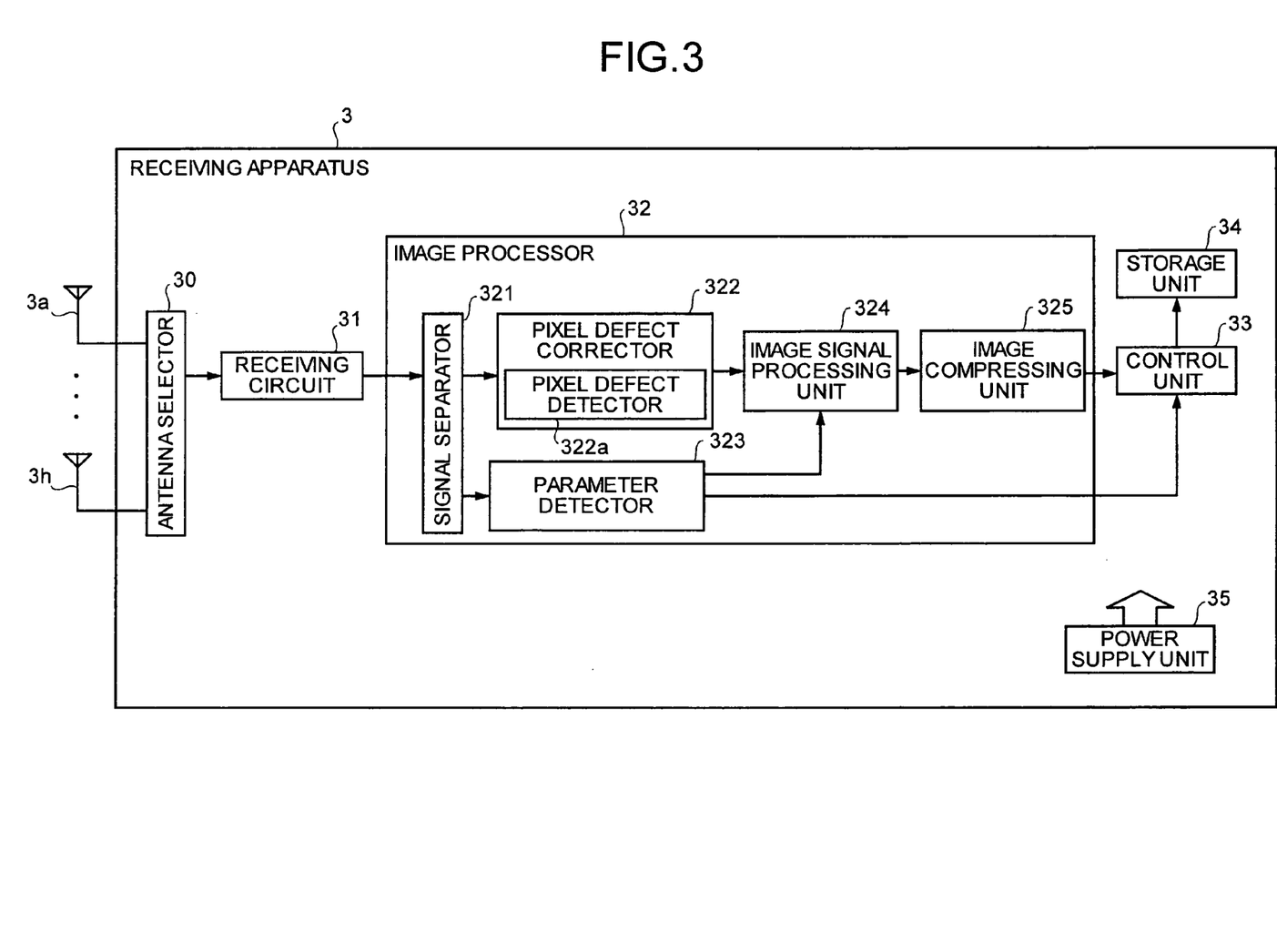
FIG. 3 is a block diagram of a configuration example of a receiving apparatus according to one embodiment of the present invention.

FIG. 3 is a block diagram of a configuration example of the receiving apparatus 3 according to one embodiment of the present invention. As shown in FIG. 3, the receiving apparatus 3 includes an antenna selector 30 that selects a receiving antenna appropriate for receiving the radio signal, out of a plurality of receiving antennas 3a to 3h, a receiving circuit 31 for performing a modulating process or the like on the radio signal received via any one of the receiving antennas 3a to 3h, and an image processor 32 that performs an image-data-related process based on the signal fed from the receiving circuit 31. The receiving apparatus 3 further includes a control unit 33 that controls driving of each element of the receiving apparatus 3, a storage unit 34 that stores extracted information such as the image data, and a power supply unit 35 that supplies driving power to each element of the receiving apparatus 3.

The antenna selector 30 is electrically connected to each of a plurality of receiving antennas 3a to 3h, selects any one of the receiving antennas 3a to 3h, and outputs to the receiving circuit 31 the radio signal received via the selected receiving antenna. In this case, the antenna selector 30 detects received electric-field strength of the radio signal received via each of the receiving antennas 3a to 3h, for example, and compares received electric-field strength detected so as to select a receiving antenna that has received a radio signal with the highest received electric-field strength.

The function of the receiving circuit 31 is to perform processes including a modulation process on the radio signal fed from the antenna selector 30. More specifically, when receiving the radio signal transmitted by the capsule endoscope 2, the receiving circuit 31 restores the image signal included in the radio signal. The receiving circuit 31 outputs the obtained image signal to the image processor 32.

The function of the image processor 32 is to perform a process in which a pixel defect of the image data included in the image signal fed from the receiving circuit 31 is detected and corrected, and a process in which image data of a frame unit is generated based on the corrected image data. As shown in FIG. 3, the image processor 32 includes a signal separator 321 that separates the image signal fed from the receiving circuit 31 into image data and a parameter, a pixel defect corrector 322 that detects the pixel defect of the image data separated and extracted by the signal separator 321 and corrects the pixel defect, a parameter detector 323 that detects the WB data and the capsule ID data based on the parameter separated and extracted by the signal separator 321, an image signal processing unit 324 that generates the image data of a frame unit based on the image data corrected by the pixel defect corrector 322 and the WB data detected by the parameter detector 323, and an image compressing unit 325 that performs a predetermined image compression process on the image data generated by the image signal processing unit 324.

Figure 4:
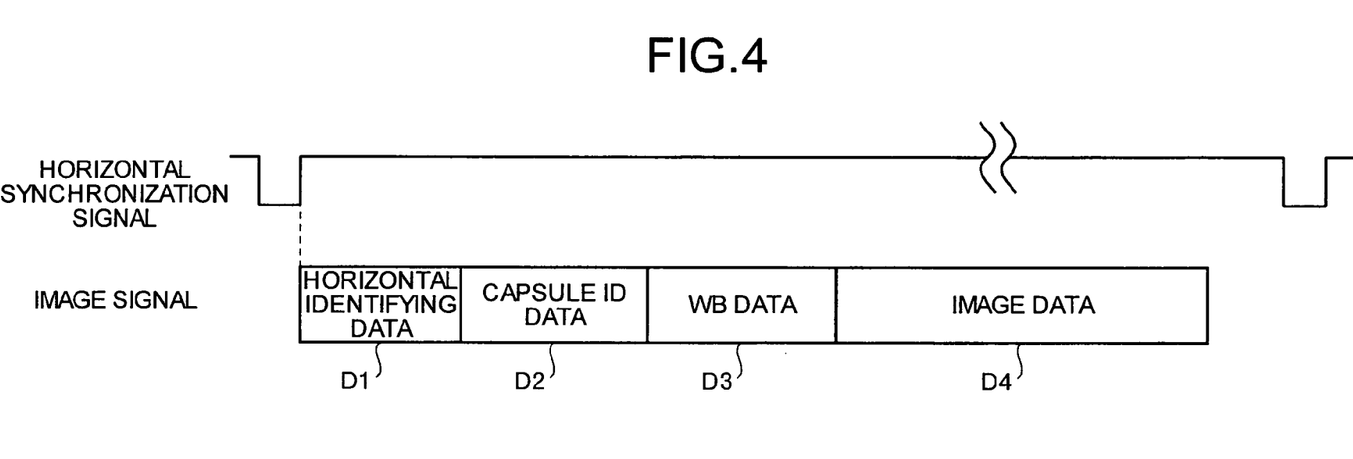
FIG. 4 is a schematic diagram of and example of a data format of a unit of transmission of an image signal.

The function of the signal separator 321 is to separate the image signal fed from the receiving circuit 31 into the image data and the parameter. When the image signal is an image signal generated and output by the capsule endoscope 2, the image data imaged by the capsule endoscope 2, and the parameter such as the capsule ID data and the WB data, for example, are superimposed to the image signal, as explained above. FIG. 4 is a schematic diagram of a data format of the transmission data. The data format serves as a unit of transmission, when the capsule endoscope 2 transmits the image signal. The unit of transmission corresponds to one line of the image imaged by the imaging unit 22. The unit configuration includes horizontal identifying data D1 that indicates the head of a horizontal line included in one frame of image data, capsule ID data D2 superimposed immediately after the horizontal identifying data D1, WB data D3 superimposed immediately after the capsule ID data D2, and non-compressed image data D4 superimposed immediately after the WB data D3, as shown in FIG. 4. In this case, the signal separator 321 uses a predetermined horizontal synchronization signal so as to detect the horizontal identifying data D1, whereby the image signal is synchronized in the horizontal direction. Thereafter, the signal separator 321 extracts and separates the capsule ID data D2 and the WB data D3 as a parameter signal, and outputs the parameter signal to the parameter detector 323. At the same time, the signal separator 321 extracts and separates the image data D4 as an image data signal, and outputs the image data signal to the pixel defect corrector 322. The signal separator 321 performs the signal separation process on all image signals received from the receiving circuit 31.

The function of the pixel defect corrector 322 is to detect and correct the pixel defect of the image data separated and extracted by the signal separator 321. The pixel defect occurs due to a local crystal defect, an electrostatic fracture, aging, among others, of a semiconductor of a solid-state image pick-up device such as CCD used in the imaging unit 22. In a pixel in which the defect occurs, a certain bias is superimposed on an electric signal that corresponds to an incident light amount and the image is output as it is. Thus, the pixel defect appears on the picked-up image as a white spot or a black spot. That is, the pixel defect appears as a pixel-based error. The pixel defect corrector 332 performs a process to detect and correct a pixel in which such a pixel defect, that is, the error of a pixel unit occurs. The pixel defect corrector 322 has a pixel defect detector 322a that detects the pixel defect of the image data separated and extracted by the signal separator 321. The pixel defect detector 322a detects the pixel defect based on a pixel value of each pixel that configures the image data fed from the signal separator 321.

For example, the pixel defect detector 322a detects the pixel value of each pixel horizontally aligned in image data of a line unit, compares the pixel value of each pixel with a pixel value of an adjacent pixel of the same color located to the right or the left of the pertinent pixel. When the comparison results exceed a predetermined threshold value, the pixel defect detector 322a detects the relevant pixel as the pixel defect. When the radio signal output by the capsule endoscope 2 is subjected to noise or the like before it is received by the receiving apparatus 3, and a communication error occurs in the image data portion of the radio signal, an error of a pixel unit similar to the pixel defect occurs on the image. Consequently, the image data received by the receiving apparatus 3 includes both the pixel defect specific to the imaging unit 22 of the capsule endoscope 2, and the pixel defect, which is the error of a pixel unit, caused by the communication error. Therefore, the pixel defect detector 322a detects not only the pixel defect present in a fixed pixel position specific to the imaging unit 22 of the capsule endoscope 2 but also a communication error of a pixel unit occurring in a random pixel position of the image data due to the noise interference on the radio signal before the radio signal output by the capsule endoscope 2 is received via any one of the receiving antennas 3a to 3h, similarly to the above mentioned pixel defect. The pixel defect detector 322a detects the pixel value of each pixel vertically aligned in the image data across a plurality of lines, compares the pixel value of each pixel with a pixel value of an adjacent pixel of the same color located above or below the pertinent pixel. When the comparison results exceed a predetermined threshold value, the pixel defect detector 322a can detect the pixel as the pixel defect.

The pixel defect corrector 322 performs a process for correcting the pixel defect detected by the pixel defect detector 322a. For example, the pixel defect corrector 322 may correct the pixel defect by replacing the pixel value of the pixel, which is detected as the pixel defect, with an average value of the pixels of the same color horizontally adjacent to the pertinent pixel The pixel defect corrector 322 can also correct the pixel defect by replacing the pixel value of the defective pixel with the average value of the pixels of the same color vertically adjacent to the defective pixel. Thus, the pixel defect detector 322a detects the pixel defect specific to the imaging unit 22, and detects the pixel defect, which is an error of a pixel unit, caused by the communication error due to the noise interference. Therefore, the pixel defect corrector 322 can correct pixel defect specific to the imaging unit 22 and further correct a dynamic pixel defect caused by the noise interference, that is, a communication error of a pixel unit. Thereafter, the pixel defect corrector 322 sequentially outputs to the image signal processing unit 324 the image data of which pixel defect has been corrected.

Though the pixel defect detector 322a dynamically detects the pixel defect specific to the imaging unit 22, the pixel defect detector 322a can be configured to detect the specific pixel defect based on address information that indicates a pixel defect position in which the specific pixel defect occurs. That is, the pixel defect position in which the specific pixel defect occurs is detected beforehand at the time of manufacturing the capsule endoscope 2, and the address information of the pixel that indicates the detected pixel defect position is stored in the parameter storage unit 25 of the capsule endoscope 2. The capsule endoscope 2 is to wirelessly transmit the address information by superimposing it on the image signal as in the case of the above explained WB data and capsule ID data. The receiving apparatus 3 is to receive the address information together with the image signal from the capsule endoscope 2. The pixel defect detector 322a can detect the specific pixel defect based on the received address information.

Further, the pixel defect detector 322a can be configured to perform a process for detecting the pixel defect as explained above on image data in a unit of a plurality of frames. When the pixel defect is detected in the same pixel position in the image data in a unit of a plurality of frames, the pixel defect detector 322a is to store the same pixel position as a pixel position in which the pixel defect specific to the imaging unit 22 occurs, and thereafter, is not to perform a process for detecting the pixel defect regarding the pixel position. In this case, the pixel defect detector 322a can be configured to transmit to the pixel defect corrector 322 the information that indicates the stored pixel position, and the pixel defect corrector 322 can be configured to correct the pixel defect in the pixel position based on this information even when the pixel defect detector 322 does not perform the process for detecting the pixel defect. In another case, the pixel defect detector 322a can perform a control operation for correcting the pixel defect in the pixel position on the pixel defect corrector 322 based on the stored pixel position.

The function of the parameter detector 323 is to detect the WB data and the capsule ID data based on the parameter signal fed from the signal separator 321. The parameter detector 323 outputs to the image signal processing unit 324 the WB data detected based on the received parameter signal. The parameter detector 323 outputs to the control unit 33 the detected capsule ID data based on the received parameter signal.

The function of the image signal processing unit 324 is to perform a predetermined image process based on the image data corrected by the pixel defect corrector 322, the WB data detected by the parameter detector 323, and other data, and to generate the image data by each frame. Specifically, the image signal processing unit 324 performs a white balance correction process for correcting the white balance of each image data based on each image data sequentially fed from the pixel defect corrector 322 and the WB data fed from the parameter detector 323. The image signal processing unit 324 further performs a gamma correction process, and image processes such as an outline emphasizing process, on each image data fed from the pixel defect corrector 322.

The image signal processing unit 324 further generates image data (received image data) of a frame unit by a predetermined number of image data in which a predetermined image process is performed. When the capsule endoscope 2 transmits the image data of the predetermined number of frame lines, the image signal processing unit 324 generates the received image data by the image data of a line unit of which number of lines is the same as the predetermined number of frame lines. In this case, the number of frame lines is the number of horizontal lines included in one frame. That is, one frame of the image data is configured by the image data of a line unit of which number of lines is the same as the number of the frame lines.

The received image data generated by the image signal processing unit 324 is sequentially input to the image compressing unit 325. The image compressing unit 325 performs a predetermined image compression process on each received image data sequentially fed from the image signal processing unit 324, and compresses each received image data. The image signal processing unit 324 outputs to the control unit 33 the compressed received image data.

In the meantime, the storage unit 34, to which the above portable recording medium 5 is detachably attached, sequentially writes into the portable recording medium 5 information based on a control operation of the control unit 33, e.g., the received image data generated by the image signal processing unit 324. The storage unit 34, by itself, can be configured to store the information by mounting RAM or a memory IC such as a flash memory.

The power supply unit 35 supplies each element of the receiving apparatus 3 with driving power even when the receiving apparatus 3 is carried by the subject 1, as shown in FIG. 1. Examples of the power supply unit 35 include a cell battery, a lithium-ion secondary battery, a nickel hydride battery. In another case, the power supply unit 35 can be rechargeable.

Figure 5:
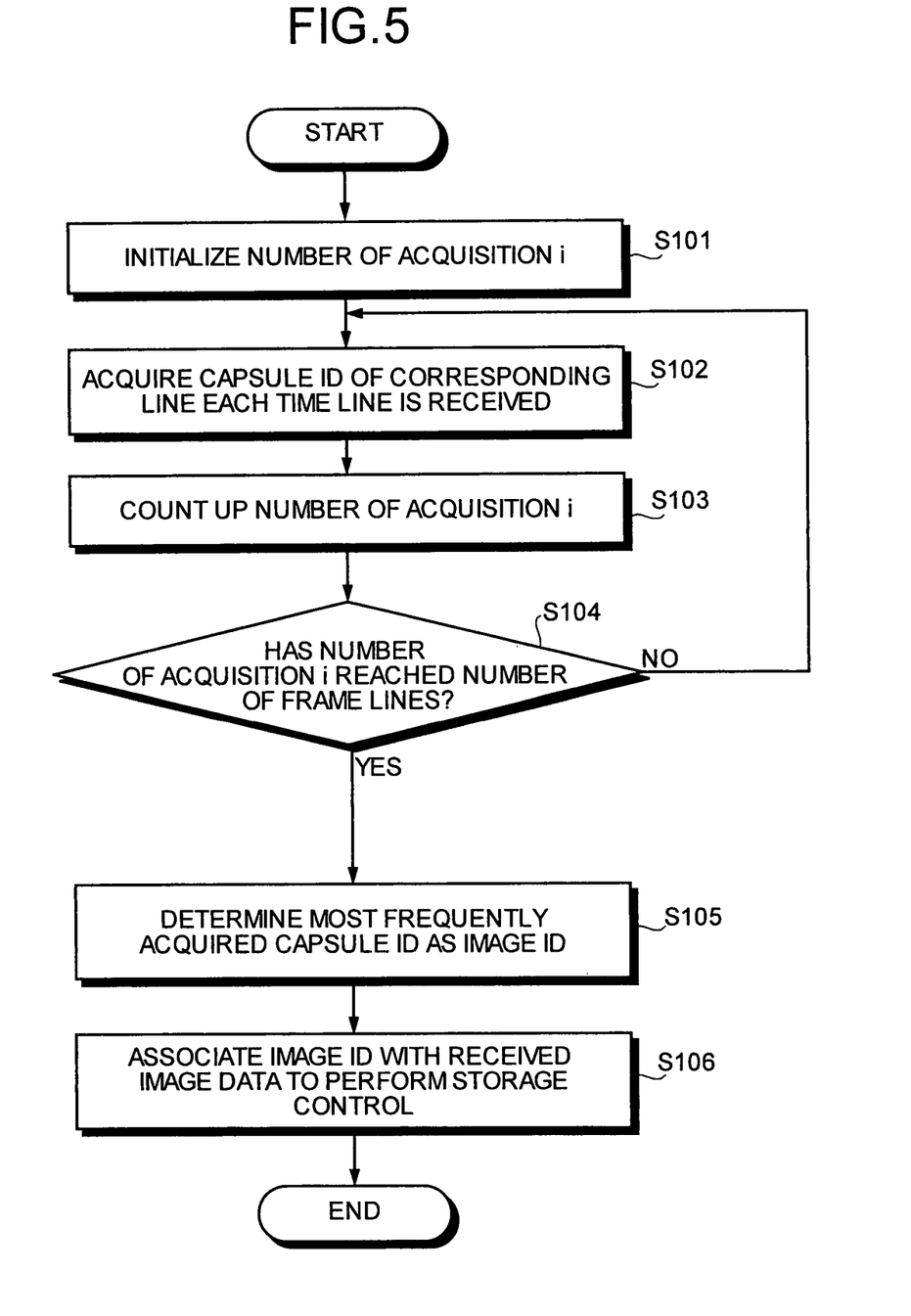
FIG. 5 is a flowchart exemplifying a process procedure in which an image ID and received image data are associated with each other and stored in a storage unit.

The control unit 33 is achieved by a CPU (Central Processing Unit) that executes various kinds of processing programs, a ROM in which various kinds of processing programs or the like are recorded beforehand, and an RAM that stores an operation parameter for each process, the capsule ID data, and the like. The control unit 33 controls driving of each element of the receiving apparatus 3. The control unit 33 allows the storage unit 34 to store the received image data or the like fed from the image compressing unit 325, for example. In this case, the control unit 33 determines an image ID for specifying the capsule endoscope that has transmitted the image data based on the capsule ID data, which is detected by the parameter detector 323, by each image data of a line unit, and allows the storage unit 34 to store the determined image ID and the received image data that is received in a corresponding manner. FIG. 5 is a flowchart for exemplifying a process procedure in which the determined image ID and the received image data are associated with each other and stored in the storage unit 34.

The control unit 33 performs the process procedure shown in FIG. 5 at every time it starts receiving an image in a frame, determines the image ID of each received frame based on the capsule ID detected by the parameter detector 323 at every time of receiving each line of the image, performs a control operation for allowing the determined image ID and the received image data to be associated with each other, and stores the data into the storage unit 34. That is, the control unit 33 firstly initializes the number of acquisitions i that indicates the number of lines that the capsule ID is acquired, and sets the number of acquisitions i to "0" (step S101).

The control unit 33 then acquires the capsule ID based on the capsule ID data D2 that is detected by the parameter detector 323 at every time of receiving the line, and is subsequent to the horizontal identifying data D1 (step S102). In this case, the control unit 33 stores the acquired capsule ID in a memory area (not shown) of the control unit 33. The control unit 33 further performs a process for counting up the number of acquisitions i, and adds "1" to the number of acquisitions i (step S103).

Thereafter, the control unit 33 repeats the process procedures of the above steps S102 to S104 until the number of acquisitions i reaches the number of acquisitions n that is previously set. In this case, the number of acquisitions n corresponds to the number of vertical lines of one frame of the image data (hereinafter, "the number of frame lines") transmitted by the capsule endoscope 2. That is, the control unit 33 determines whether the number of acquisitions i reaches the number of frame lines. When determining that the number of acquisitions i does not reach the number of frame lines, that is, the number of acquisitions n (step S104, No), the control unit 33 repeats the process procedures of the step S102 onwards.

On the other hand, when the control unit 33 determines that the number of acquisitions i reaches the number of frame lines, that is, the number of acquisitions n (step S104, Yes), the control unit 33 determines, out of the acquired capsule IDs, the most received capsule ID, that is, the most frequently acquired capsule ID, as the image ID of the received image data (step S105).

Thereafter, the control unit 33 allows the received image data fed from the image compressing unit 325 and the image ID determined in the step S107 to be associated with each other, and transfers them to the storage unit 34. The control unit 33 controls the storage unit 34 so that it stores the received image data with which the image ID is associated (step S106).

In this case, there is a case that the control unit 33 receives the capsule ID data in which a communication error such as garbled characters caused by the noise interference described above, out of the capsule ID data received for the same number of times as the number of acquisitions n from the parameter detector 323. Even so, the control unit 33 can determine the capsule ID as the above most frequently acquired capsule ID based on the rest of the capsule ID data received in a normal state. That is, the control unit 33 can correct a communication error of a frame unit regarding the capsule ID data, the control unit 33 can allow the image ID that corresponds to the normal capsule ID and the received image data to be associated with each other to be stored in the storage unit 34.

On the other hand, the control unit 33 can also determine whether the received image data generated by the image signal processing unit 324 is an effective image or an ineffective image based on the capsule ID data, which is detected by the parameter detector 323, by each image data of a line unit. The effective image means effective image data in examining the subject 1, that is, normal image data imaged by the capsule endoscope 2. In contrast, the ineffective image means image data not effective in examining the subject 1, that is, abnormal image data in which the communication error caused by the noise interference described above occurs, for example.

Figure 6:
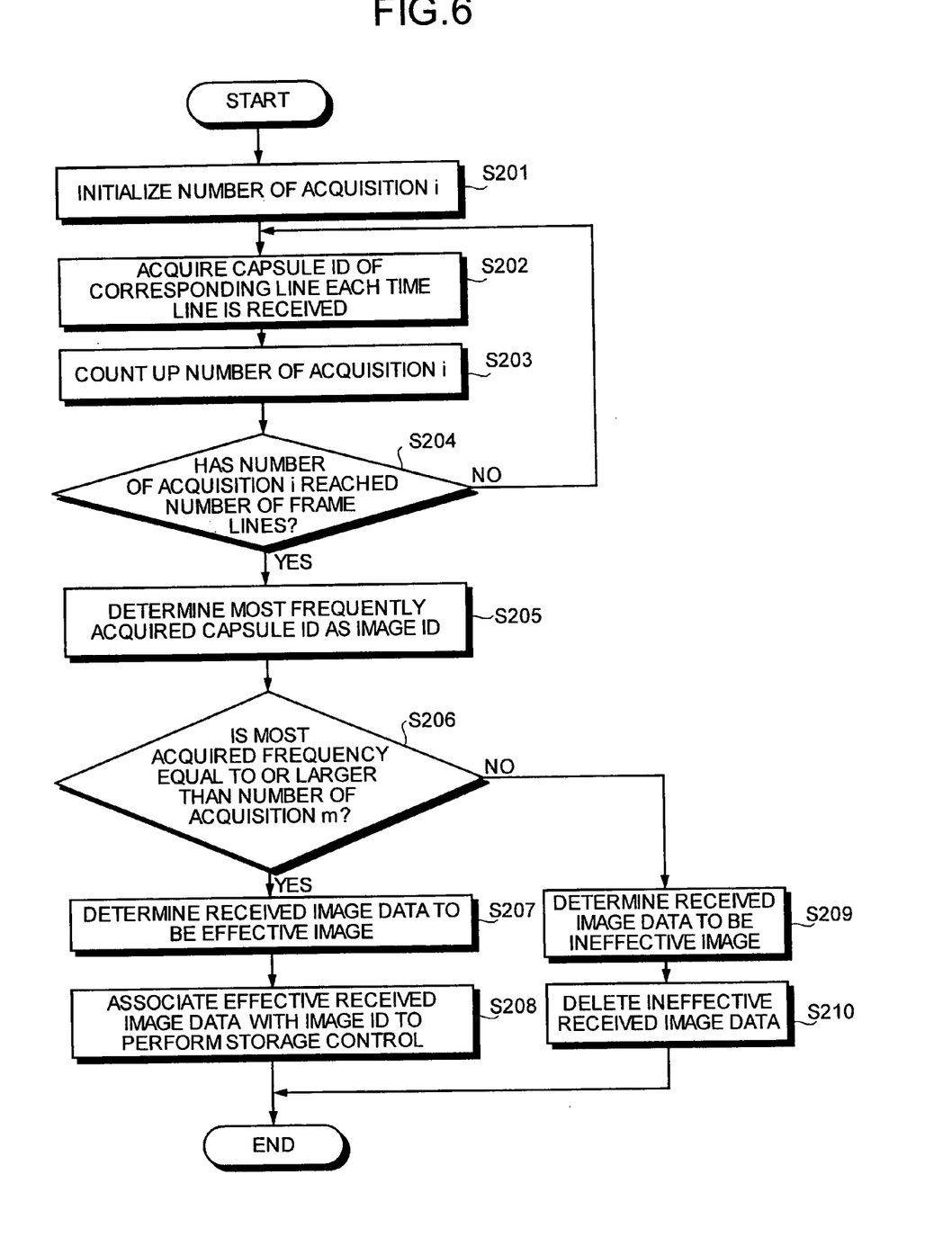
FIG. 6 is a flowchart exemplifying a process procedure in which the received image data is determined to be an effective image or an ineffective image.

FIG. 6 is a flowchart for exemplifying a process procedure in which the acquired received image data is determined to be an effective image or an ineffective image, and the received image data determined to be the effective image is stored in the storage unit 34. In FIG. 6, the control unit 33 performs a process procedure similar to the above steps S101 to S106 so as to acquire the capsule ID as much as the number of acquisitions n, and determines the most frequently acquired capsule ID, out of all the capsule IDs, as the image ID (steps S201 to S205).

The control unit 33 then makes a comparison between the most acquired frequency of the capsule ID that is associated with the image ID determined in the step S207 and the number of acquisitions m, as determination reference information, recorded beforehand in the control unit 33. When the most acquired frequency exceeds the number of acquisitions m (step S206, Yes), the control unit 33 determines that the received image data generated by the image signal processing unit 324 is the effective image (step S207). Thereafter, the control unit 33 allows the effective received image data determined to be the effective image and the image ID determined in the step S205 described above to be associated with each other, and transfers them to the storage unit 34. The control unit 33 controls the storage unit 34 so that it stores the effective received image data to which the image ID is corresponded (step S208).

On the other hand, the control unit 33 makes a comparison between the above most acquired frequency and the number of acquisitions m. When the most acquired frequency is less than the number of acquisitions m (step S206, No), the control unit 33 determines that the received image data generated by the image signal processing unit 324 is the ineffective image (step S209). Thereafter, the control unit 33 deletes the ineffective received image data determined to be the ineffective image (step S210). The storage unit 34 is not made to store this ineffective image data.

In this case, the control unit 33 can determine, out of capsule IDs based on the capsule ID data received from the parameter detector 323 for the same number of times as the number of acquisitions n, the normal same capsule ID that is most frequently acquired, as the above most frequently acquired capsule ID. Because of this determination, although there is a case that the control unit 33 receives the capsule ID data in which the communication error such as garbled characters caused by the noise interference described above occurs, the control unit 33 can correct this communication error by determining the most frequently acquired capsule ID as the image ID of the received image data.

The control unit 33 further determines that the acquired received image data is the effective image or the ineffective image, based on the results in which the most acquired frequency of the capsule ID that corresponds to the determined image ID and the number of acquisitions m, which is the determination reference, are compared. Because of this, although there is a case that a communication error occurs because the radio signal from the capsule endoscope 2 is mixed with a different radio signal from another capsule endoscope, and the receiving apparatus 3 receives this radio signal, the control unit 33 can determine that the received image data is the effective image or the ineffective image as follows: the received image data that includes the image data of a line unit that corresponds to the most frequently acquired capsule ID for the same number of times or more as the number of acquisitions m, that is, the image data that includes the image data in which the image data of the predetermined number of lines m or more from the same capsule endoscope is included in the received image, is the effective image, and the rest of the received image data is the ineffective image. Accordingly, the control unit 33 can correct such a communication error of a frame unit, and distinguish between the effective received image data determined to be the effective image and the ineffective received image data so as to sequentially store them in the storage unit 34.

Preferably, the above number of acquisitions m is the major part of the number of frame lines n of the received image data generated by the image signal processing unit 324. As a result, the control unit 33 can determine that the received image data that includes the image data of a line unit that corresponds to the most frequently acquired capsule ID for the major part of the number of frame lines n is the effective image, and can improve the determination accuracy between the effective image and the ineffective image accordingly.

In the embodiment of the present invention, the capsule ID data is used as the specifying information for specifying the capsule endoscope 2. The present invention, however, is not limited thereto. Information specific to the capsule endoscope 2 such as the WB data can be used as the specifying information. In this case, the control unit 33 can determine the image ID based on the information specific to the capsule endoscope 2.

In the embodiment of the present invention, when the capsule endoscope 2 generates the image signal, the capsule ID data is superimposed immediately after the horizontal identifying data, and the WB data is superimposed immediately after the capsule ID data. The present invention, however, is not limited thereto. The parameter such as the capsule ID, the WB data, and the like can be superimposed in a region between the horizontal identifying data and the image data, and its order can be constant in a series of image data.

In the embodiment of the present invention, the received image data determined to be the ineffective image is deleted and not stored in the storage unit 34. The present invention, however, is not limited thereto. The received image data determined to be the ineffective image and ineffective image specifying information such as the ID code that indicates the ineffective image are associated with each other, and this received image data can be stored in the storage unit 34 in association with the ineffective image specifying information.

In this manner, as explained above, the embodiment of the present invention employs a configuration that the pixel defect is detected based on the pixel value of each pixel that configures each received image data at every time the receiving apparatus receives the image data transmitted by the capsule endoscope, and an interpolation process is performed based on the pixel value of the pixel of the same color horizontally adjacent to the pixel in which the pixel defect is detected, whereby the pixel defect is corrected. Therefore, it is possible to achieve the receiving apparatus capable of detecting the pixel defect specific to the image pick-up device of the capsule endoscope, without increasing power consumption of the capsule endoscope, detecting also the dynamic pixel defect as a communication error of a pixel unit caused by the fact that the radio signal from the capsule endoscope gathers the noise interference on its propagation path, correcting the specific pixel defect, and easily correcting the communication error of a pixel unit that appears as the dynamic pixel defect caused by the noise interference. It is also possible to achieve the capsule endoscope system that uses the receiving apparatus.

In the capsule endoscope system and the receiving apparatus using the same, the specifying information of the capsule endoscope is acquired by each image data of a line unit that configures the image data of a frame unit imaged by the capsule endoscope, and the image specifying information for specifying the image data of a frame unit is determined based on the acquisition number of the specifying information. Therefore, even when the communication error such as garbled characters caused by the noise interference described above occurs in one portion of the specifying information of the capsule endoscope, it is possible to easily allow the image specifying information that corresponds to the specifying information of this capsule endoscope and the image data of a frame unit to correspond to each other, whereby it is possible to correct the communication error such as garbled characters.

The acquired image data of a frame unit is determined whether the effective image or the ineffective image based on the acquisition number of the specifying information. Therefore, even when there is a communication error caused by interference between the image data of a frame unit imaged by the capsule endoscope, and the image data imaged by a different capsule endoscope, which is noise, it is still possible to determine as the effective image of the image data of a frame unit that includes the image data to be acquired for a predetermined number of lines, and determine the rest of the image data as the ineffective image. Accordingly, it becomes possible to distinguish between the effective image and the ineffective image by each acquired image data of a frame unit for sequentially storing, and easily correct the communication error of a frame unit caused by the interference. This leads to prevention of the ineffective image caused by the interference from being used for observation in the display device 4.

INDUSTRIAL APPLICABILITY

As explained above, the capsule endoscope system according to the present invention is effective for acquiring the intra-subject image data imaged by the capsule endoscope. Particularly, the present invention is suitable for a capsule endoscope system capable of easily correcting the communication error without increasing the power consumption of the capsule endoscope.

The invention claimed is:

1. A capsule endoscope system comprising:
  a capsule endoscope that is configured to image image data of a subject by an imaging unit, and to transmit a radio signal that includes the image data of which a pixel defect is not corrected; and
  a receiving apparatus that is configured to receive the radio signal via receiving antennas, and to acquire the image data based on the received radio signal, wherein
  the receiving apparatus includes
  a pixel defect corrector that is configured to detect and correct a pixel defect of the image data; and
  a pixel defect detector that is configured to detect the pixel defect present in a fixed pixel position specific to the imaging unit of the capsule endoscope and a communication error of a pixel unit occurring in a random pixel position of the image data due to noise interference on the radio signal before the radio signal output by the capsule endoscope is received via any one of the receiving antennas, wherein the pixel defect detector is configured to detect a pixel value of each pixel horizontally aligned in the image data of a line unit, compare the pixel value of each pixel with a pixel value of an adjacent pixel of the same color located to the right or the left of a pertinent pixel, and detect the pertinent pixel as the pixel defect when the comparison results exceed a predetermined threshold value, and the pixel defect detector is configured, when the pixel defect is detected in a particular pixel position in the image data in a unit of plurality of frames, to store the particular pixel position as a pixel position in which the pixel defect specific to the imaging unit occurs, to transmit to the pixel defect corrector information that indicates the stored pixel position, and thereafter not to perform a process of detecting the pixel defect regarding the pixel position, wherein the pixel defect corrector is configured to correct the pixel defect in the pixel position based on the information without the pixel defect detector performing a process of detecting the pixel defect having the stored pixel position.

2. The capsule endoscope system according to claim 1, wherein the capsule endoscope transmits the radio signal in an uncompressed state.

* * * * *